(12) United States Patent
Boehm

(10) Patent No.: US 9,888,980 B2
(45) Date of Patent: Feb. 13, 2018

(54) NOZZLE HEAD, HAND PIECE AND POWDER JET DEVICE FOR APPLYING A DENTAL MATERIAL

(71) Applicant: 3M INNOVATIVE PROPERTIES COMPANY, St. Paul, MN (US)

(72) Inventor: Andreas J. Boehm, Reichling (DE)

(73) Assignee: 3M Innovative Properties Company, Saint Paul, MN (US)

( * ) Notice: Subject to any disclaimer, the term of this patent is extended or adjusted under 35 U.S.C. 154(b) by 27 days.

(21) Appl. No.: 14/652,393

(22) PCT Filed: Dec. 10, 2013

(86) PCT No.: PCT/US2013/074125
§ 371 (c)(1),
(2) Date: Jun. 15, 2015

(87) PCT Pub. No.: WO2014/099495
PCT Pub. Date: Jun. 26, 2014

(65) Prior Publication Data
US 2015/0335395 A1    Nov. 26, 2015

(30) Foreign Application Priority Data

Dec. 17, 2012  (EP) ..................... 12197567

(51) Int. Cl.
*A61C 3/025* (2006.01)
*A61C 1/08* (2006.01)
*A61C 17/02* (2006.01)

(52) U.S. Cl.
CPC .............. *A61C 3/025* (2013.01); *A61C 1/087* (2013.01); *A61C 17/02* (2013.01)

(58) Field of Classification Search
CPC ................................ A61C 3/025; A61C 17/02
See application file for complete search history.

(56) References Cited

U.S. PATENT DOCUMENTS 2,529,004 A    11/1950  Eley
3,939,599 A    2/1976   Henry
(Continued)

FOREIGN PATENT DOCUMENTS

CA    1225262    8/1987
CH    656524     7/1986
(Continued)

OTHER PUBLICATIONS

Haffajee, "The effect of SRP on the clinical and microbiological parameters of periodontal diseases," Journal of Clinical Periodontology, 1997, vol. 24, No. 5, pp. 324-334.
(Continued)

*Primary Examiner* — Michael D Abreu

(57) ABSTRACT

A nozzle head (12) for a powder jet device (10) for use in applying dental material, the nozzle head (12) comprising: a first portion (16) and a second portion (18) transitioning into one another; the first portion (16) adjacent a first end (20) of the nozzle head (12) having a coupling (22) for removably connecting the nozzle head (12) to a hand piece (14) of the powder jet device (10); the second portion (18) adjacent a second end (26) of the nozzle head (12) forming a nozzle outlet (28) for the dental material; the second portion (18) comprising at least a first fluid channel (30) which is formed between the nozzle outlet (28) and a channel inlet (32); wherein the channel inlet (32) is arranged at the transition (34) between the first portion (16) and the second portion (18) between the nozzle outlet (28) and the coupling (22).

19 Claims, 3 Drawing Sheets

(56) References Cited

U.S. PATENT DOCUMENTS

| | | | |
|---|---|---|---|
| 3,972,123 A | 8/1976 | Black | |
| 4,078,558 A | 3/1978 | Woog | |
| 4,184,258 A | 1/1980 | Barrington | |
| 4,248,589 A | 2/1981 | Lewis | |
| 4,266,535 A | 5/1981 | Moret | |
| 4,308,996 A * | 1/1982 | Rotolico | B05B 7/205 239/290 |
| 4,492,575 A | 1/1985 | Mabille | |
| 4,595,365 A | 6/1986 | Edel | |
| 4,676,749 A | 6/1987 | Mabille | |
| 5,120,219 A | 6/1992 | De Farcy | |
| 5,158,455 A | 10/1992 | Bailey | |
| 5,306,144 A | 4/1994 | Hibst | |
| 5,833,456 A | 11/1998 | Davis | |
| 5,857,851 A | 1/1999 | Chavanne | |
| 6,054,119 A | 4/2000 | Hurme | |
| 6,126,444 A | 10/2000 | Horiguchi | |
| 6,238,211 B1 | 5/2001 | Esrock | |
| 6,293,856 B1 | 9/2001 | Hertz | |
| 6,485,304 B2 | 11/2002 | Beerstecher | |
| 6,648,644 B1 | 11/2003 | Flemmig | |
| 6,884,070 B2 | 4/2005 | Cevey | |
| 7,083,411 B2 | 8/2006 | Flemmig | |
| 7,175,430 B1 | 2/2007 | Gasser | |
| 7,762,812 B2 | 7/2010 | Pichat | |
| 7,980,923 B2 | 7/2011 | Olmo | |
| 8,210,846 B2 | 7/2012 | Duineveld | |
| 2001/0021496 A1 | 9/2001 | Aumuller | |
| 2002/0123020 A1 | 9/2002 | Aumuller | |
| 2002/0127513 A1 | 9/2002 | Bachmann | |
| 2003/0008263 A1 | 1/2003 | Cook | |
| 2003/0129560 A1 | 7/2003 | Atkin | |
| 2004/0166474 A1 | 8/2004 | Gugel | |
| 2006/0121411 A1 | 6/2006 | Wiek | |
| 2007/0042316 A1* | 2/2007 | Pichat | A61C 3/025 433/80 |
| 2009/0317758 A1 | 12/2009 | Duineveld | |
| 2010/0029757 A1 | 2/2010 | Hellerbrand | |
| 2010/0151413 A1* | 6/2010 | Andersson | A61C 3/025 433/88 |
| 2010/0297576 A1 | 11/2010 | Donnet | |
| 2011/0117523 A1 | 5/2011 | Cook | |
| 2011/0281238 A1 | 11/2011 | Cook | |
| 2012/0329005 A1* | 12/2012 | Olmo | A61C 3/025 433/88 |
| 2013/0266908 A1* | 10/2013 | Casabonne | A61C 3/025 433/88 |

FOREIGN PATENT DOCUMENTS

| | | |
|---|---|---|
| CN | 2032047 | 2/1989 |
| CN | 2321545 | 6/1999 |
| CN | 2440591 | 8/2001 |
| DE | 3538324 | 5/1986 |
| DE | 4123019 | 1/1993 |
| EP | 0097288 | 1/1984 |
| EP | 0119021 | 9/1984 |
| EP | 0119735 | 9/1984 |
| EP | 0163610 | 12/1985 |
| EP | 0299229 | 1/1989 |
| EP | 1145689 | 10/2001 |
| EP | 1468659 | 10/2004 |
| EP | 2070505 | 6/2009 |
| ES | 8800833 | 2/1988 |
| FR | 2575062 | 6/1986 |
| FR | 2583630 | 12/1986 |
| FR | 2588182 | 4/1987 |
| FR | 2599244 | 12/1987 |
| GB | 1211150 | 11/1970 |
| GB | 1480594 | 7/1977 |
| GB | 2026359 | 2/1980 |
| JP | 58041550 | 3/1983 |
| JP | 11104148 | 4/1999 |
| JP | 2000-051235 | 2/2000 |
| JP | 2000-083966 | 3/2000 |
| JP | 2001-204741 | 7/2001 |
| JP | 2002-153490 | 5/2002 |
| JP | 2002-165806 | 6/2002 |
| JP | 2002-209911 | 7/2002 |
| JP | 2003-116880 | 4/2003 |
| KR | 20100008362 | 8/2010 |
| WO | 1989-07932 | 9/1989 |
| WO | 1994-00078 | 1/1994 |
| WO | 1996-12447 | 5/1996 |
| WO | 1997-04741 | 2/1997 |
| WO | 1998-08906 | 3/1998 |
| WO | 1999-20197 | 4/1999 |
| WO | 2000-53154 | 9/2000 |
| WO | 2001-36159 | 5/2001 |
| WO | 2001-72273 | 10/2001 |
| WO | 2002-13721 | 2/2002 |
| WO | 2002-74180 | 9/2002 |
| WO | 2003-003934 | 1/2003 |
| WO | 2003-011164 | 2/2003 |
| WO | 2003-043519 | 5/2003 |
| WO | 2003-075784 | 9/2003 |
| WO | 2004-075770 | 9/2004 |
| WO | 2005-007008 | 1/2005 |
| WO | 2005-106734 | 11/2005 |
| WO | 2005-115645 | 12/2005 |
| WO | 2007-034612 | 3/2007 |
| WO | 2007-134336 | 11/2007 |
| WO | 2009-148907 | 12/2009 |
| WO | 2010-010360 | 1/2010 |
| WO | 2011-123123 | 10/2011 |
| WO | 2013-191903 | 12/2013 |
| WO | 2014-099490 | 6/2014 |
| WO | 2014-099800 | 6/2014 |

OTHER PUBLICATIONS

Axelsson, "The significance of maintenance care in the treatment of periodontal disease," Journal of Clinical Periodontology, 1981, vol. 8, No. 4, pp. 281-294.

Zappa, "Root Substance Removal by Scaling and Root Planing" Journal of Periodontology, Dec. 1991, vol. 62, No. 12, pp. 750-754.

Boyde, Airpolishing Effects on Enamel, Dentine, Cement and Bone, British Dental Journal, Apr. 21, 1984, vol. 156, pp. 287-291.

Flemmig,"Working Parameters of a Magnetostrictive Ultrasonic Seale Influencing Root Substance Removal In Vitro," Journal of Periodontology 1998, vol. 69, pp. 547-553.

Sauro, "Dentine desensitization induced by prophylactic and airpolishing procedures: An in vitro dentine permeability and confocal microscopy study," Journal of Dentistry 2010, vol. 38, pp. 411-422.

International Search Report for PCT International Application No. PCT/US2013/074125, dated Mar. 4, 2014, 4 pages.

* cited by examiner

NOZZLE HEAD, HAND PIECE AND POWDER JET DEVICE FOR APPLYING A DENTAL MATERIAL

FIELD OF THE INVENTION

The present invention relates to a nozzle head, a hand piece and a powder jet device for use in applying a dental material to a desired location, for example the tooth structure of a patient.

BACKGROUND ART

In dentistry powder jet devices are currently used for applying a fluid stream of abrasive particles, air and water to the tooth structure of a patient, for example for cleaning or pretreating the tooth surfaces.

Generally, a powder jet device may comprise a nozzle head through which the fluid stream can be delivered. Typically the fluid stream contains powder particles which are dispersed and entrained by an air stream guided through a powder containing chamber, and a liquid optionally added to the air/powder mixture, for example through a separate nozzle. In a device of that type used for cleaning tooth surfaces the powder material often comprises dental abrasive particles, and the liquid is normally water.

Examples of a nozzle head for powder jet devices for use in the field of dentistry are described in U.S. Pat. No. 4,676,749 (Mabille) or U.S. Pat. No. 7,762,812 (Pichat et al.). Some powder materials, when delivered through a nozzle of a powder jet device, may tend to block the nozzle. That may be the case if the powder comes into contact with moisture because the powder may become damp and flow less freely than when it is dry. In a more extreme case, the powder may be intended to form a hardenable paste or gel when mixed with the fluid and can, therefore be expected to block the nozzle unless removed. For example, the nozzle head of the device shown in U.S. Pat. No. 4,676,749 has long and curved supply canals having a relatively narrow inner diameter. Such canal may be hard to clean when it comes to powder clogging.

Some powder jet devices for use in the field of dentistry are provided with disposable nozzles as shown in U.S. Pat. No. 4,676,749 for example. Although available devices provide certain advantages there is still a desire for a device which operates reliably with different types of powder and which is relatively easy to maintain. Further such a device desirably is relatively inexpensive and meets hygiene requirements in dentistry.

SUMMARY OF THE INVENTION

The present invention provides a nozzle head for a powder jet device for use in applying dental material. The nozzle head comprises a first portion and a second portion which transition into one another. The first portion adjacent a first end of the nozzle head has a coupling for removably connecting the nozzle head to a hand piece of the powder jet device. The second portion adjacent a second end of the nozzle head forms a nozzle outlet for the dental material. The second portion comprises at least a first fluid channel which is formed between the nozzle outlet and a channel inlet. The channel inlet is arranged at the transition between the first portion and the second portion between the nozzle outlet and the coupling.

The expression "the first portion and the second portion transition into one anther" in the sense of the present invention is to be understood in that the first portion and the second portion directly contact one another. The first portion and the second portion may be connected to one another. Preferably, the first portion and the second portion are integrally manufactured (in particular formed in one piece).

The nozzle head may be integrally formed by injection molding. Because the channel inlet is arranged at the transition between the first portion and the second portion between the nozzle outlet and the coupling, a sealing joint between the nozzle head and the hand piece may be placed in the first portion adjacent the joint between the first and second portion and offset from the first end. Thus a stream of air with powder dispersed therein may be delivered close toward the nozzle outlet. On the other hand the nozzle head is adapted such that the first portion covers non-replaceable portions of the hand piece and protects these from getting into contact with a patient when the nozzle head is placed on the hand piece.

The transition of the first portion and the second portion is preferably arranged closer to the nozzle outlet than to the coupling. Accordingly, the transition of the first portion and the second portion is further offset towards the nozzle outlet. The first portion may extend along a first longitudinal axis and the second portion may extend along a center axis. The first portion may longer than the second portion and may be formed straight or essentially straight. Thus the nozzle head may be relatively easy to manufacture by injection molding. The longitudinal axis and the center axis are preferably inclined relative to each other. The inclination is preferably such that the longitudinal axis and the center axis are oriented at an angle which is between a concentric and perpendicular angle of the longitudinal axis and the center axis relative to each other. Further in the flowing it is referred to the external angle (as opposed to the included angle) and thus to the greater of the angles formed between longitudinal axis and the center axis.

The first fluid channel may extend along the second longitudinal axis. Thus, the first fluid channel may be formed straight and may be manufactured by injection molding. The second portion may comprise at least a second fluid channel. The second fluid channel may be arranged parallel to the first fluid channel, for example may extend coaxially to the first fluid channel over at least a portion of its length. This arrangement provides separate ducts for two media such as water and powder/air dispersion to the nozzle outlet.

The second portion may further comprise at least a third fluid channel. The second fluid channel and the third fluid channel may be arranged side by side with the first fluid channel therebetween. This arrangement further preferably provides a relatively homogeneous aerosol curtain around the air/powder dispersion emitted from the first fluid channel.

The second portion may comprise a first annular or groove space arranged coaxially to the first fluid channel. The second fluid channel and the third fluid channel may open into the first annular space. The groove preferably opens adjacent the nozzle outlet.

The first portion may comprise a fourth fluid channel and a fifth fluid channel. The fourth fluid channel is preferably in fluid communication with the second fluid channel and the fifth fluid channel is preferably in fluid communication with the third fluid channel.

The coupling of the first portion may connectable to the hand piece such that the nozzle head is rotatable relative to the hand piece. Thus, the disposable nozzle head may be freely rotatable (for example over 360 degrees) in any angle desired by an operator. This may particularly facilitate the handling of the device.

The present invention further provides a hand piece for a powder jet device for use in applying dental material. The hand piece comprises a body, an outer tube arranged within the body and at least one first fluid tube protruding from the outer tube.

The hand piece may comprise an outer tube and the first fluid tube may extend within the outer tube. Accordingly, the outer tube and the first fluid tube may be concentric tubes for powder/air dispersion and water transport. Further, the reusable part of the powder jet device may be straight and may not have a restriction at its end. Therefore the device may be relatively easy to clean and may help in avoiding clogging. The concentrically arrangement also allows the disposable nozzle head to be rotated by 360 degrees in any of the two directions.

One or more of the outer tube and the first fluid tube may be made of metal. Accordingly, the tubes for powder/air dispersion and water transport are part of the hand piece and can be made out of metal. Therefore, the reusable part of the powder jet device may be straight and thus relatively easy to clean and may help in avoiding clogging.

The present invention further provides a powder jet device for use in applying dental material. The powder jet device comprises a nozzle head according to any one of the above aspects or embodiments, and a hand piece according to any one of the above aspects or embodiments, wherein the nozzle head and the hand piece are removably connected to each other.

The body of the hand piece may be removably connected to the coupling of the first portion of the nozzle head, wherein the first fluid tube protrudes from the outer tube so as to extend to the transition from the first portion to the second portion such that the first fluid tube and the first fluid channel are in fluid communication with one another at the channel inlet. According to this arrangement, the first fluid tube protrudes a certain distance from the outer tube and extends deep into the nozzle head. Thus, a sealing joint between the nozzle head and the hand piece may be offset towards the nozzle outlet if compared with nozzle head known from the prior art.

The second portion may further comprise at least a second fluid channel and a third fluid channel, wherein the second fluid channel and the third fluid channel are arranged side by side with the first fluid channel therebetween. The outer tube and the first fluid tube may be arranged such that an interior space or groove is formed therebetween. The interior space may at least partially define a fluid supply line. Further the interior space may be formed such that the fluid supply line is in fluid communication with the second fluid channel and the third fluid channel. According to this arrangement, at least two media may be supplied at the same time without mixing within the nozzle head but only at the nozzle outlet. Thus, the above mentioned problem of clogging may be prevented.

The first portion may comprise a fourth fluid channel and a fifth fluid channel. The first portion of the nozzle head and the hand piece may be formed such that a second annular space or groove is formed therebetween. The fluid supply line is preferably in fluid communication with the fourth fluid channel and the fifth fluid channel within the first portion by means of the second annular space. According to this arrangement, the nozzle head may be rotated relative to the hand piece and the supply of two media is possible in each rotation position. Thus, the device may be operated in a variety of different positions.

The concentric arrangement of the nozzle head and the hand piece allows the disposable nozzle head to be rotated 360° in any angle. The fluid channels within the nozzle head may be formed by mold cores of the molding tool having an aspect ratio of smaller than 5:1. The disposable nozzle head may be locked in the hand piece at the side opposite to the nozzle outlet.

The fluid tubes of the hand piece may be formed as separate ducts for the water and the powder/air dispersion to the nozzle outlet in the molded nozzle head. A relatively homogeneous aerosol curtain around the powder air jet is preferably achieved because the water is emitted from the annular groove at the nozzle tip. The powder/air dispersion may exit from the nozzle outlet at a speed of about 300 m/s and may merge with the water to form a water/powder/air spray. The amount of water may be controlled by a control provided at the device.

For manufacturing of the angled tubes the mold cores in a mold tool may be movable from opposite sides of the nozzle orifice. Undesired holes in the finished nozzle head created by one or both of the cores may be closed by a plug, by use of a hot melt, by ultra sonic welding or by overmolding in a second step, for example via a two shot molding technique.

BRIEF DESCRIPTION OF THE FIGURES

By way of example, a powder jet device having a nozzle head and a hand piece in accordance with the invention will now be described with reference to the accompanying drawings, in which.

DETAILED DESCRIPTION OF THE INVENTION

Figure 1:
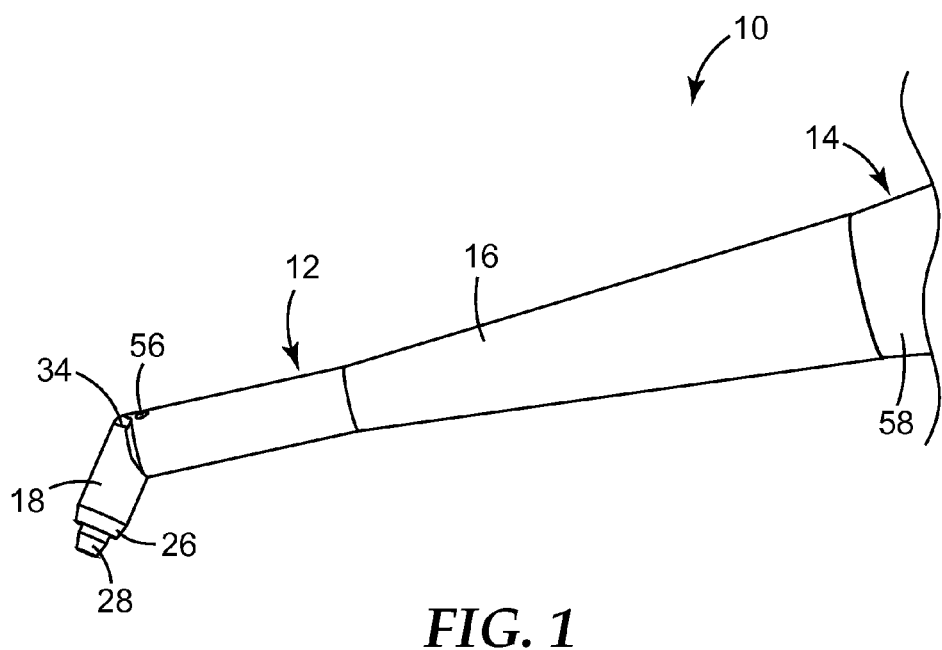
FIG. 1 is a side view of the powder jet device.
Figure 2:
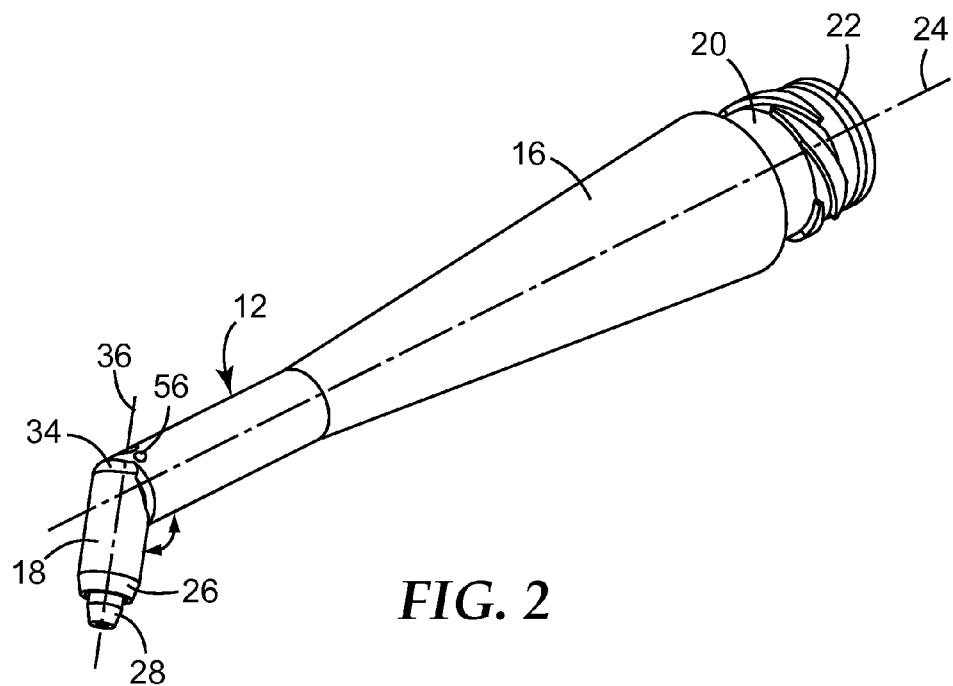
FIG. 2 is a side view of the nozzle head.

The powder jet device 10 shown in the drawings is of a type for use in the dental field for applying a powder/gas mixture and a liquid to the tooth structure of a patient. FIG. 1 shows a side view of the powder jet device 10. The device 10 comprises a nozzle head 12 and a hand piece 14 which may also serve and formed as a handgrip. The nozzle head 12 comprises a first portion 16 and a second portion 18 transitioning into one another. FIG. 2 shows a side view of the nozzle head 12. The first portion 16 adjacent a first end 20 of the nozzle head 12 has a coupling 22 for removably connecting the nozzle head 12 to the hand piece 14. The first portion 16 is removably connectable to the hand piece 14 such that the nozzle head 12 is rotatable relative to the hand piece 14. For example, the coupling 22 may be formed as a combination of a thread and an axial portion, which does not comprise any protrusions or the like, such that the thread is guided through a counter-thread (not shown) of the hand piece 14 and the nozzle head 12 is rotatable on the axial portion relative to the hand piece 14. Needless to say, alternative couplings may be applied to the nozzle head 12 and the hand piece 14, e.g. a snap-fit mechanism or the like.

The first portion 16 extends along a first longitudinal axis 24. Particularly, the first portion 16 may be formed as a tube-shaped body which is formed rotation symmetrical around the first longitudinal axis 24. It is to be noted that the first portion 16 may be a cylindrical tube or a tube being conical as shown in FIGS. 1 and 2.

Figure 3:
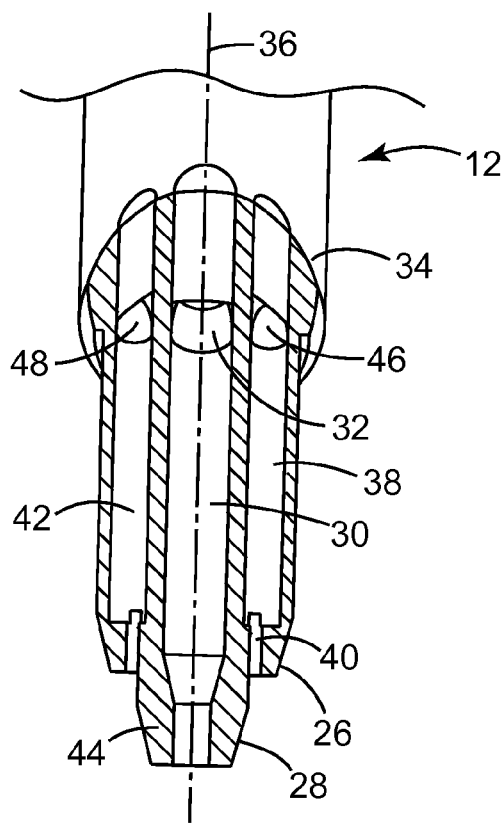
FIG. 3 is a longitudinal section of the second portion of the nozzle head.

FIG. 3 shows a longitudinal section of the second portion 18 of the nozzle head 12. The second portion 18 may be formed substantially as a stepped conical tube. The second portion 18 adjacent a second end 26 of the nozzle head 12 forms a nozzle outlet 28 for the dental material.

The second portion 18 comprises at least a first fluid channel 30. The first fluid channel 30 is formed between the nozzle outlet 28 and a channel inlet 32. The channel inlet 32, which is a first channel inlet, is arranged at the transition 34 between the first portion 16 and the second portion 18 between the nozzle outlet 28 and the coupling 22. As can be seen from FIGS. 1 and 2, the transition 34 is arranged closer to the nozzle outlet 28 than to the coupling 22. The second portion 18 is angled relative to the first longitudinal axis 24. For example, the second portion 18 extends at an angle ranging from 100 degrees to 150 degrees, for example 120 degrees, relative to the first longitudinal axis 24. The angle may be defined between the first longitudinal axis 24 and a central axis (not shown) of the second portion 18. The first fluid channel 30 is formed as a straight channel. Thus, the first fluid channel 30, which is disposed within the second portion 18, extends along a second longitudinal axis 36 which may be a central axis of the second portion 18. The second longitudinal axis 36 may is a central axis of the first fluid channel 30. The second longitudinal axis 36 extends at an angle ranging from 100 degrees to 150 degrees, for example 120 degrees, relative to the first longitudinal axis 24.

The second portion 18 further comprises at least one second fluid channel 38. The second fluid channel 38 is arranged parallel to the first fluid channel 30. The second fluid channel 38 is formed straight. A first annular space 40 is arranged coaxially to the first fluid channel 30. The first annular space 40 is arranged closer to the nozzle outlet 28 than to the transition 34. The first fluid channel 30 is formed as a channel having a constant diameter from the first channel inlet 32 to the first annular space 40. The diameter of the first fluid channel 30 decreases from the first annular space 40 to the nozzle outlet 28. For example, the diameter may decrease linearly or conically or stepped conically as shown in FIG. 3. The second fluid channel 38 opens into the first annular space 40. The second portion 18 further comprises a third fluid channel 42. The third fluid channel 42 is arranged parallel to the first fluid channel 30. The third fluid channel 42 is formed straight. The third fluid channel 42 opens into the first annular space 40. Particularly, the second fluid channel 38 and the third fluid channel 42 are arranged side by side with the first fluid channel 30 therebetween. The second portion 18 further comprises a fluid outlet 44 which is arranged coaxially to the nozzle outlet 28 and around the nozzle outlet 28. The first annular space 40 is in fluid communication with the fluid outlet 44. hus, the second fluid channel 38 and the third fluid channel 42 are in fluid communication with the fluid outlet 44 and with one another by means of the first annular space 40. The second fluid channel 38 comprises a second channel inlet 46. The second channel inlet 46 is arranged at the transition 34. The third fluid channel 42 comprises a third channel inlet 48. The third channel inlet 48 is also arranged at the transition 34. The second fluid channel 38 and the third fluid channel 42 are formed as channels having constant diameters from the second channel inlet 46 and the third channels inlet 48, respectively, to the first annular space 40.

Figure 4:
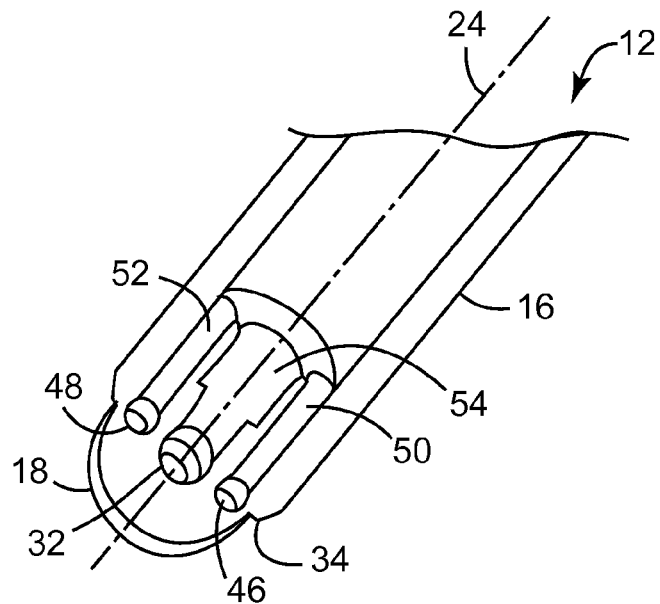
FIG. 4 is a longitudinal section of the first portion of the nozzle head.

FIG. 4 shows a longitudinal section of the first portion 16 of the nozzle head 12. The first portion 16 further comprises a fourth fluid channel 50 and a fifth fluid channel 52. The fourth fluid channel 50 and the fifth fluid channel 52 extend parallel to the first longitudinal axis 24. The fourth fluid channel 50 is in fluid communication with the second fluid channel 38 at the second channel inlet 46. The fifth fluid channel 52 is in fluid communication with the third fluid channel 42 at the third channel inlet 48. The first portion 16 further comprises an insertion portion 54 formed within the first portion 16 and coaxially with the first longitudinal axis 24. The fourth fluid channel 50 and the fifth fluid channel 52 are arranged side by side with the insertion portion 54 therebetween. The fourth fluid channel 50 and the fifth fluid channel 52 are formed as straight channels having constant diameters. The insertion portion 54 is formed as a portion whose diameter decreases in a stepped manner from the first end 20 to the first channel inlet 32. The diameter may decrease in a stepped manner as shown in FIG. 4. Particularly, the diameter of the insertion portion 54 adjacent the first channel inlet 32 is identical to the diameter of the first fluid channel 30. The diameters of the fourth fluid channel 50 and the fifth fluid channel 52 are identical to the diameters of the second fluid channel 38 and third fluid channel 42. The diameter of the insertion portion 54 is greater than the one of the fourth fluid channel 50 and the fifth fluid channel 52.

The nozzle head 12 may be made of plastics such as PP, HDPE, POM, PBT etc. and be manufactured by means of injection molding. For the production of the fluid channels 30, 38 and 42, the mold cores used for manufacturing the nozzle head 12 and the fluid channels 30, 38 and 42 are drawn out to the opposite side of the nozzle outlet 28 at the second portion 18. Accordingly, after a first step of molding, there remain holes at the opposite side of the nozzle outlet 28 adjacent the second portion 18 and in the first portion 16 close to the transition 34. The holes remaining in the first portion 16 can be closed by a second part such as plugs, with a hot melt, by ultra sonic welding or by overmolding in a second step of molding within the same mold, i.e. by means of the so-called two shot molding technique. FIGS. 1 and 2 shows exemplarily plugs 56 inserted into such holes of the fluid channels 30, 38 and 42 from a side opposite to the nozzle outlet 28. The plugs 56 are adhered or fixed to the nozzle head 12. For example, the plugs 56 may be melted to the nozzle head 12 within the fluid channels 30, 38 and 42. T he plugs 56 may extend close to the channel inlets 32, 46 and 48 but do not block the same. Similarly, the fourth fluid channel 50 and the fifth fluid channel 52 are formed by drawing out mold cores towards the first end 20.

Figure 5:
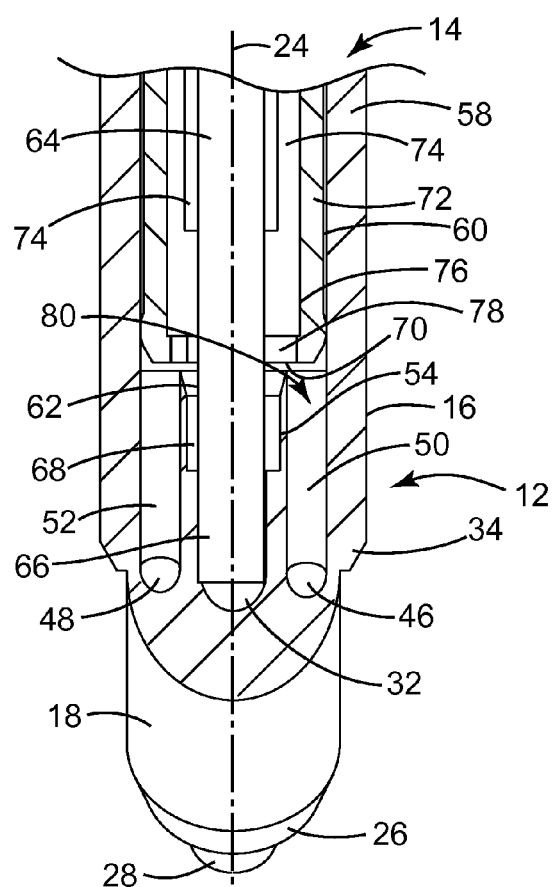
FIG. 5 is perspective view of the powder jet device and the interior thereof.

FIG. 5 shows a longitudinal section of the powder jet device 10 with the nozzle head 12 connected to the hand piece 14. The hand piece 14 comprises a body 58, an outer tube 60 arranged within the body 58 and at least one first fluid tube 62 protruding from the outer tube 60. The first fluid tube 62 additionally extends within the outer tube 60. Accordingly, the outer tube 60 and the first fluid tube 62 are concentric tubes. Particularly, the first fluid tube 62 comprises an inner portion 64, which is disposed within the outer tube 60, and an outer portion 66, which is disposed outside from the outer tube 60. The first fluid tube 62 is made of metal. The first fluid tube 62 is formed straight.

The first fluid tube 62 is partially enclosed by a first sealing member 68 such that the first sealing member 68 completely covers an outer surface of the inner portion 64 of the first fluid tube 62 in a circumferential direction and in an axial direction. Further, the first sealing member 68 partially covers the outer portion 66 of the first fluid tube 62 such that the outer portion 66 adjacent an axial end face 70 of the outer tube 60 is completely covered in a circumferential direction and the outer portion 66 penetrates the first sealing member 68 in a direction facing away from the outer tube 60.

A second sealing member 72 is disposed within the outer tube 60 such that the second sealing member 72 covers an inner wall of the outer tube 60 and the axial end face 70. The second sealing member 72 contacts the first sealing member 68 only adjacent the axial end face 70 such that an interior space 74 is formed between the first sealing member 68 and the second sealing member 72. The interior space 74 at least partially defines a fluid supply line 76 as will be explained in more detail below. Adjacent the axial end face 70, the first sealing member 68 penetrates the second sealing member 72. The second sealing member 72 comprises an opening 78 adjacent the axial end face 70.

Figure 6:
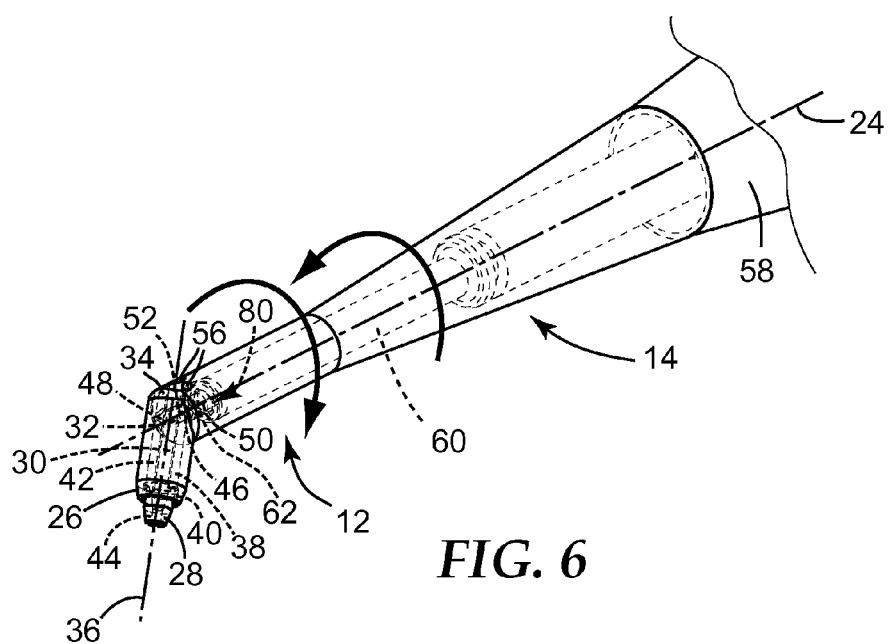
FIG. 6 is a longitudinal section of the powder jet device.

FIG. 6 shows a perspective view of the powder jet device 10 with the interior thereof. In a state in which the nozzle head 12 is connected to the hand piece 14 by means of the coupling 22, the outer tube 60 is inserted into the first portion 16 of the nozzle head 12. The nozzle head 12 is rotatable by 360 degrees relative to the hand piece 14 around the outer tube 60 as indicated by means of arrows. More particularly, the first fluid tube 62 is inserted into the insertion portion 54 and extends to the transition 34 from the first portion 16 to the second portion 18. Thus, the first fluid tube 62 engages the first channel inlet 32 such that the first fluid tube 62 and the first fluid channel 30 are in fluid communication at the first channel inlet 32. Further, the hand piece 14 is inserted into the first portion 16 such that a second annular space 80 is formed between the axial end 70 and the fourth fluid channel 50 as well as the fifth fluid channel 52. Thus, the interior space 74 and the fourth fluid channel 50 as well as the fifth fluid channel 52 are in fluid communication with one another by means of the opening 78 and the second annular space 80. As the fourth fluid channel 50 is in fluid communication with the second fluid channel 38 and the fifth fluid channel 52 is in fluid communication with the third fluid channel 42, the fluid supply line 76 is in fluid communication with the second fluid channel 38 and the third fluid channel 42. In this connected state, the first sealing member 68 engages the nozzle head 12 in the first portion 16. The first sealing member 68 prevents any fluid supplied through the first fluid tube 62 from leaking such that the supplied fluid is reliably supplied through the first fluid tube 62 into the first fluid channel 30. Similarly, the second sealing member 72 prevents any fluid supplied through the interior space 74 from leaking such that the fluid supplied through the interior space 74 is reliably supplied to the fourth fluid channel 50 and the fifth fluid channel 52.

For example, powder may be supplied by means of air from a powder reservoir (not shown) through the first fluid tube 62 into the first fluid channel 30 and exits the nozzle head 12 through the nozzle outlet 28. A liquid, e.g. water, may be supplied from a liquid reservoir (not shown) through the fluid supply line 76 partially formed by the interior space 74, exits the fluid supply line 76 at the opening 78, flows through the second annular space 80, flows through the fourth fluid channel 50 and the fifth fluid channel 52, enters the second fluid channel 38 and the third fluid channel 42 at the second channel inlet 46 and the third channel inlet 48, and flows together within the first annular space 40 and exits the nozzle head 12 through the fluid outlet 44. The fluids mentioned, i.e. the powder/air mixture and the liquid, may be independently or together supplied. The nozzle head 12 may be designed such that the two media mentioned are not mixed within the nozzle head 12 but shortly after leaving the nozzle outlet 28 and the fluid outlet 44 such that a clogging may be prevented. Of course, the nozzle head 12 may be a disposable nozzle head 12 which will be replaced after use.

The powder jet device 10 can be used to apply various dental materials. For example, the powder jet device 10 will be used to apply a hardenable dental composition to the tooth structure of a patient. The dental composition may, for example, harden into a highly-viscous paste or gel and may, for example, be a dental retraction composition used to retract soft dental tissue away from hard dental tissue and thereby open the sulcus temporarily, for example to enable a dental impression to be taken. The dental composition may formed by combining a suitable powder material with a liquid, for example water or a salt solution. Examples of powder materials that the device can be used to apply are those described in European patent application No. 07122768.0, filed 10 Dec. 2007 and entitled "Dental Retraction Composition, Production thereof and Use of a Powder Jet Device for Dental Retraction".

In use of the powder jet device 10, the powder material required for the dental retraction composition is contained within the powder reservoir, and the interior space 74 is connected to a pressurized source of the liquid, for example by means of a supply line of the powder jet device 10 (not shown). A gas supply line (not shown) is connected to a pressurized source of a gas suitable for dental use and for transporting the powder material from the reservoir to the hand piece 14 and the nozzle head 12. The gas may, for example, be air. The sources of pressurized liquid and gas, and the controls for regulating their supply, are not shown and may be at any suitable remote location. Alternatively, the supply may be regulated by a trigger or a similar device at the hand piece 14.

The pressurized gas delivered into the powder reservoir produces a powder/gas mixture in the reservoir, which passes along the first fluid tube 62 in the hand piece 14 towards the nozzle head 12 from where it is discharged through the nozzle outlet 28. While that is happening, pressurized liquid may be supplied towards the nozzle head 12 from where it is discharged through the fluid outlet 44 and is directed, along with the air/powder mixture, to the tooth structure of the patient where the powder and the liquid combine to form the hardenable dental composition.

It will be understood that the above-described use of the powder jet device 10 to apply a dental retraction composition is one example only of the uses of powder jet devices in the dental field. A powder jet device 10 having a nozzle head 12 in accordance with the invention could be use to apply a variety of dental compositions, some of which may not be intended to harden or to remain in position after application, some of which may need to be cured after application, and others of which may comprise components that react chemically with one another after application. A powder jet device 10 having a nozzle head 12 in accordance with the invention may, for example, be used to apply a mixture of abrasive particles and water for cleaning the surfaces of a patient's teeth.

Although a powder jet device 10 typically uses a stream of gas to transport the powder material, that is not essential and a stream of liquid could be used instead, when appropriate. When a stream of gas is used, any appropriate gas can be selected that is not detrimental to the patient, and does not react in an unwanted manner with the powder material or any other materials with which it may come into contact. Typically, however, air is preferred.

In some cases, there may be no need to discharge a liquid from the nozzle head 12 of the powder jet device 10 at the same time as the powder/gas mixture. In that case, the liquid supply to the nozzle head 12 can be omitted. Even when a liquid is to be applied with the gas/powder mixture, it need not be applied from the nozzle head 12 of the powder jet device but could be applied from a separate source. It is also not essential for the liquid to be applied at exactly the same time as the powder/gas mixture: in some cases, for example, it may be more appropriate for the application of the liquid not to commence until the flow of the powder/gas mixture is already established. When a liquid is applied with the powder/gas mixture, any appropriate liquid can be selected that is not detrimental to the patient, and functions in the required manner when in combination with the powder material. The liquid may, for example, be required to dissolve the powder material applied by the powder jet device 10, or to combine with it to form a dispersion, an emulsion or a gel, or to cause the powder to swell. Examples of other liquids that may be selected are alcohols and ketones. Typically, however, water is preferred.

The invention claimed is:

1. A nozzle head for a powder jet device for use in applying dental material, the nozzle head comprising:
   a first portion and a second portion transitioning into one another;
   the first portion adjacent a first end of the nozzle head having a coupling for removably connecting the nozzle head to a hand piece of the powder jet device;
   the second portion adjacent a second end of the nozzle head forming a nozzle outlet for the dental material;
   the second portion comprising at least a first fluid channel which is formed between the nozzle outlet and a channel inlet defined by the nozzle head;
   wherein the channel inlet is arranged at the transition between the first portion and the second portion between the nozzle outlet and the coupling; and
   wherein the nozzle head defines an interior channel configured to receive a protruding portion defined by the hand piece.

2. A powder jet device for use in applying dental material, comprising:
   a nozzle head according to claim 1; and
   the hand piece, the hand piece comprising:
      a body;
      an outer tube arranged within the body; and
      at least one first fluid tube protruding from the outer tube, wherein the nozzle head and the hand piece are removably connected to each other.

3. The powder jet device of claim 2, wherein the body of the hand piece is removably connected to the coupling of the first portion of the nozzle head, wherein the first fluid tube protrudes from the outer tube so as to extend to the transition from the first portion to the second portion such that the first fluid tube and the first fluid channel are in fluid communication with one another at the channel inlet, and wherein the protruding portion comprises the first fluid tube.

4. The powder jet device of claim 3, wherein the second portion further comprises at least a second fluid channel and a third fluid channel, wherein the second fluid channel and the third fluid channel are arranged side by side with the first fluid channel therebetween, wherein the outer tube and the first fluid tube are arranged such that an interior space is formed therebetween, wherein the interior space at least partially defines a fluid supply line, wherein the interior space is formed such that the fluid supply line is in fluid communication with the second fluid channel and the third fluid channel.

5. The powder jet device of claim 3, wherein the first portion comprises a fourth fluid channel and a fifth fluid channel, wherein the first portion of the nozzle head and the hand piece are formed such that a second annular space is formed therebetween, wherein the fluid supply line is in fluid communication with the fourth fluid channel and the fifth fluid channel within the first portion by means of the second annular space.

6. The powder jet device of claim 2, further comprising a powder reservoir configured to contain a powder material, wherein the powder reservoir is fluidically connected to the nozzle head.

7. The powder jet device of claim 6, wherein the nozzle head is configured to discharge at least the powder material through the nozzle outlet.

8. The powder jet device of claim 6, wherein the powder reservoir is fluidically connected to the nozzle head through the at least one fluid tube of the hand piece.

9. The nozzle head of claim 1, wherein the second portion further comprises at least a third fluid channel, wherein the second fluid channel and the third fluid channel are arranged side by side with the first fluid channel therebetween.

10. The nozzle head of claim 9, wherein the second portion comprises a first annular space arranged coaxially to the first fluid channel, wherein the second fluid channel and the third fluid channel open into the first annular space.

11. The nozzle head of claim 9, wherein the first portion comprises a fourth fluid channel and a fifth fluid channel, wherein the fourth fluid channel is in fluid communication with the second fluid channel and the fifth fluid channel is in fluid communication with the third fluid channel.

12. The nozzle head of claim 1, wherein the first portion extends along a first longitudinal axis and the second portion is angled relative to the first longitudinal axis.

13. The nozzle head of claim 12, wherein the first fluid channel extends along a second longitudinal axis angled relative to the first longitudinal axis.

14. The nozzle head of claim 1, wherein the transition of the first portion and the second portion is arranged closer to the nozzle outlet than to the coupling.

15. The nozzle head of claim 1, wherein the second portion comprises at least one second fluid channel arranged parallel to the first fluid channel.

16. The nozzle head of claim 1, wherein the coupling of the first portion is connectable to the hand piece such that the nozzle head is rotatable relative to the hand piece.

17. The nozzle head of claim 1, wherein the nozzle head is injection molded.

18. The nozzle head of claim 1, wherein the first portion and second portion are formed in one piece.

19. The nozzle head of claim 1, wherein the nozzle head is configured to discharge at least a powder material through the nozzle outlet.

* * * * *

UNITED STATES PATENT AND TRADEMARK OFFICE
CERTIFICATE OF CORRECTION

PATENT NO. : 9,888,980 B2
APPLICATION NO. : 14/652393
DATED : February 13, 2018
INVENTOR(S) : Boehm Page 1 of 1

It is certified that error appears in the above-identified patent and that said Letters Patent is hereby corrected as shown below:

In the Specification

Column 2
Line 15, delete "non-replaceaple" and insert -- non-replaceable --, therefor.

Column 5
Lines 12-34, delete "The second portion 18 comprises at least a first fluid channel 30. The first fluid channel 30 is formed between the nozzle outlet 28 and a channel inlet 32. The channel inlet 32, which is a first channel inlet, is arranged at the transition 34 between the first portion 16 and the second portion 18 between the nozzle outlet 28 and the coupling 22. As can be seen from FIGS. 1 and 2, the transition 34 is arranged closer to the nozzle outlet 28 than to the coupling 22. The second portion 18 is angled relative to the first longitudinal axis 24. For example, the second portion 18 extends at an angle ranging from 100 degrees to 150 degrees, for example 120 degrees, relative to the first longitudinal axis 24. The angle may be defined between the first longitudinal axis 24 and a central axis (not shown) of the second portion 18. The first fluid channel 30 is formed as a straight channel. Thus, the first fluid channel 30, which is disposed within the second portion 18, extends along a second longitudinal axis 36 which may be a central axis of the second portion 18. The second longitudinal axis 36 may is a central axis of the first fluid channel 30. The second longitudinal axis 36 extends at an angle ranging from 100 degrees to 150 degrees, for example 120 degrees, relative to the first longitudinal axis 24." and insert the same on Column 5, Line 11, as a continuation of the same paragraph.
Line 58, delete "hus," and insert -- Thus --, therefor.

Column 6
Line 49, delete "T he" and insert -- The --, therefor.

Signed and Sealed this
Eighteenth Day of September, 2018

Andrei Iancu
*Director of the United States Patent and Trademark Office*